United States Patent [19]

Gamboni et al.

[11] 4,236,006

[45] Nov. 25, 1980

[54] PREPARATION OF QUINAZOLIN-2(1H)-ONES

[75] Inventors: Guido Gamboni, Allschwil; Walter Schmid, Muttenz; Alfred Sutter, Birsfelden, all of Switzerland

[73] Assignee: Sandoz Ltd., Basel, Switzerland

[21] Appl. No.: 8,328

[22] Filed: Feb. 1, 1979

Related U.S. Application Data

[63] Continuation of Ser. No. 861,426, Dec. 13, 1977, abandoned.

[30] Foreign Application Priority Data

Dec. 13, 1976 [CH] Switzerland .............................. 15619

[51] Int. Cl.$^3$ ................. C07D 239/82; A61K 31/505
[52] U.S. Cl. ..................................... 544/286; 544/250
[58] Field of Search ............................... 544/286, 250

[56] References Cited

U.S. PATENT DOCUMENTS

| | | | |
|---|---|---|---|
| 3,547,921 | 12/1970 | Hardtmann et al. | 544/286 |
| 3,551,427 | 12/1970 | Ott | 544/286 |
| 3,642,897 | 2/1972 | Hardtmann | 544/286 |
| 3,793,324 | 2/1974 | Denzer | 544/286 |

Primary Examiner—Donald G. Daus
Assistant Examiner—James H. Turnipseed
Attorney, Agent, or Firm—Gerald D. Sharkin; Richard E. Vila

[57] ABSTRACT

The invention provides a process for the production of 4-phenyl-2(1H)-quinazolinones by cyclising a corresponding 2-aminobenzophenone with urea or an alkylcarbamate in the presence of an aromatic acid. The products are known anti-inflammatory agents.

7 Claims, No Drawings

PREPARATION OF QUINAZOLIN-2(1H)-ONES

This is a continuation, of application Ser. No. 861,426 filed Dec. 13, 1977 now abandoned.

The present invention relates to quinazolinone derivatives. More precisely, this invention provides a process for the production of 4-phenyl-2(1H)-quinazolin-ones by cyclisation of the corresponding 2-aminobenzophenones with urea or an alkyl carbamate, characterised in that the cyclisation is effected in the presence of an aromatic acid.

Suitable aromatic acids include benzoic acid and o- or p-methylbenzoic acid, preferably benzoic acid. The aromatic acid is preferably employed in amounts of at least 1 mol, preferably 3 to 6 mols, of acid per mol of 2-aminobenzophenone derivative. A plurality of aromatic acids may be employed, but preferably a single aromatic acid is used, especially in the case of the benzoic acid. Suitably alkyl carbamates include $C_{1-5}$ alkyl carbamates, particularly methyl carbamate. The cyclisation is preferably effected with an alkyl carbamate.

The reaction is conveniently effected in the presence or absence of an inert organic solvent. Where a solvent is used, aromatic hydrocarbons, such as toluene, xylene or cumol, are preferred. The process is suitably effected at temperatures of 120° to 180 °C., preferably from 120° to 160° C., more preferably 140° to 160° C., especially 140 to 150°C, most preferably at the reflux temperature of the reaction mixture.

The process according to the invention is particularly suitable for the production of the known 4-phenyl-2(1H)-quinazolinones of formula I,

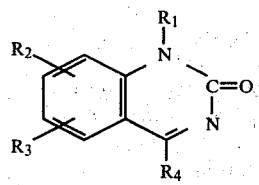

wherein $R_1$ is $C_{1-5}$ alkyl other than tertiary alkyl, in which the tert. carbon atom is directly bound to the ring nitrogen atom; allyl or propargyl, and either $R_2$ and $R_3$ are the same or different and each signifies hydrogen, fluorine, chlorine, bromine, $C_{1-3}$-alkyl, -aklylthio or -alkoxy, nitro or trifluoromethyl, with the proviso that no more than one of $R_2$ and $R_3$ signifies alkylthio, nitro or trifluoromethyl, or $R_2$ and $R_3$ together signify 6,7-methylenedioxy, $R_4$ signifies a radical of formula II,

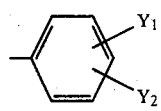

wherein $Y_1$ and $Y_2$ may be the same or different and each signifies hydrogen, fluorine, chlorine, bromine, $C_{1-3}$-alkyl or -alkoxy, or trifluoromethyl, with the proviso that no more than one of $Y_1$ and $Y_2$ signifies trifluoromethyl.

In accordance with the invention, the 4-phenyl-2(1H)-quinazolinones of formula I are obtained by cyclising 2-aminobenzophenones of formula III,

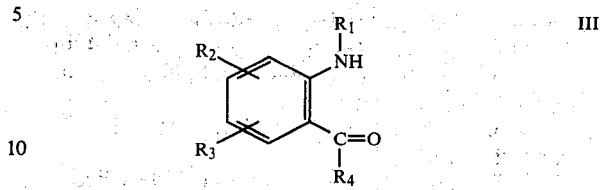

wherein $R_1$, $R_2$, $R_3$ and $R_4$ are as defined above, with urea or an alkyl carbamate in the presence of an aromatic acid.

The compounds of formula I are known compounds indicated for use as, for example, anti-inflammatory agents.

The preferred compounds of formula I are those, wherein $R_1$, $R_2$, $R_3$ and $R_4$ have the following significances:

$R_1$ = alkyl, particularly isopropyl;
either $R_2$ = hdyrogen, chlorine, alkyl, particularly methyl, or alkoxy, particularly methoxy, preferably alkyl, especially 7-alkyl,
and $R_3$ = hydrogen;
or $R_2$ and $R_3$ = 6,7-methylenedioxy;
$R_4$ = phenyl, or halophenyl, especially fluorophenyl, in particular 4-fluorophenyl.

The most preferred compounds are those having a combination of the above preferred significances.

The cyclisation of 2-aminobenzophenones with urea or alkyl carbamates to produce 4-phenyl-2(1H)-quinazolinones is generally known and it is also known to effect the urea cyclisation in the presence of alkanoic acids and to effect the alkylcarbamate cyclisation in the presence of Lewis acids. The improvement of the present invention, namely the use of aromatic acids, has not previously been proposed and leads to a series of advantages, for example ecological advantages, lower starting material requirements, higher yields and lower temperature and, therefore, energy requirements. The avoidance of the use of Lewis acids, in particular zinc chloride, eliminates corrosion problems and enables the cyclisation to be effected in steel reactors.

The following Examples illustrate the invention.

EXAMPLE 1

1-Isopropyl-4-phenyl-7-methyl-2(1H)-quinazolinone

To a solution of 100 g of 2-N-isopropylamino-4-methylbenzophenone in 50 ml of toluene, are added 90 g of urea and 200 g of benzoic acid and the resulting mixture is heated at reflux for 8 hours. 500 ml of toluene is then added and the mixture is made alkaline with caustic soda solution, the temperature being maintained at about 80° C. The toluene phase is separated, washed until neutral with hot water and then cooled, the title compound, m.p. 140°-143° C., crystallising out.

EXAMPLE 2

1-Isopropyl-4-phenyl-7-methyl-2(1H)-quinazolinone

To a solution of 100 g of 2-N-isopropylamino-4-methyl-benzophenone in 80 ml of xylene are added 60 g of methyl carbamate and 160 g of benzoic acid and the resulting mixture is heated at reflux for 8 hours. The 500 ml of toluene is added to the residue mixture and is worked up as in Example 1 to obtain the title compound, m.p. 140°–143° C.

EXAMPLE 3

In manner analogous to that described in Examples 1 or 2, and by employing appropriate starting materials in approximately equivalent amounts, the following compounds may be obtained:
(a) 1-Isopropyl-4-(4-fluorophenyly)-7-methyl-2(1H)-quinazolinone, m.p. 172°–174° C.,
(b) 1-isopropyl-4-(4-fluorophenyl)-6,7-methylenedioxy-2(1H)-quinazolinone, m.p. 238°–240° C.,
(c) 1-isopropyl-4-phenyl-6,7-methylenedioxy-2(1H)-quinazolinone, m.p. 187°–191° C.

What is claimed is:
1. In a process for the production of 4-phenyl-2(1H)-quinazolinones by cyclisation of the corresponding 2-aminobenzophenone with an alkyl carbamate, the improvement characterised in that the cyclisation is effected at a temperature of from 120° C. to 180° C. in the presence of at least one mole per mole of 2-aminobenzophenone of an aromatic acid selected from the group consisting of benzoic acid, o-methylbenzoic acid, p-methylbenzoic acid and mixtures thereof.

2. A process for the production of a compound of formula I,

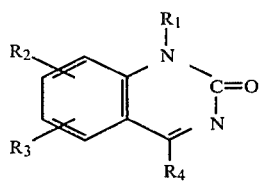

wherein
$R_1$ is $C_{1-5}$ alkyl other than tertiary alkyl, in which the tert. carbon atom is directly bound to the ring nitrogen atom; allyl or propargyl,
and either $R_2$ and $R_3$ are the same or different and each signifies hydrogen, fluorine, chlorine, bromine, $C_{1-3}$-alkyl, -alkylthio or -alkoxy, nitro or trifluoromethyl, with the proviso that no more than one of $R_2$ and $R_3$ signifies alkylthio, nitro or trifluoromethyl, or $R_2$ and $R_3$ together signify 6,7-methylenedioxy, $R_4$ signifies a radical of formula II,

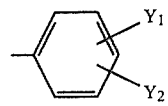

wherein
$Y_1$ and $Y_2$ may be the same or different and each signifies hydrogen, fluorine, chlorine, bromine, $C_{1-3}$-alkyl or -alkoxy, or trifluoromethyl, with the proviso that no more than one of $Y_1$ and $Y_2$ signifies trifluoromethyl,
comprising cyclising a 2-aminobenzophenone of formula III,

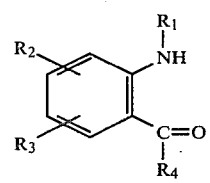

wherein $R_1$, $R_2$, $R_3$ and $R_4$ are as defined above, with an alkyl carbamate at a temperature of from 120° C. to 180° C. in the presence of at least one mole per mole of 2-aminobenzophenone of an aromatic acid selected from the group consisting of benzoic acid, o-methylbenzoic acid, p-methylbenzoic acid and mixtures thereof.

3. A process according to Claim 2, for the production of 1-isopropyl-4-phenyl-7-methyl-2(1H)-quinazolinone.

4. A process according to claim 2, for the production of 1-isopropyl-4-(4-fluorophenyl)-7-methyl-2(1H)-quinazolinone.

5. A process according to claim 1, in which the aromatic acid is benzoic acid.

6. A process according to claim 1, in which the aromatic acid is employed in a quantity of 3 or 6 moles per mole of the 2-aminobenzophenone.

7. A process according to claim 1, in which the cyclisation is effected at a temperature of from 120° to 160° C.

* * * * *